United States Patent
Rathinasabapathi et al.

(10) Patent No.: US 8,748,696 B2
(45) Date of Patent: Jun. 10, 2014

(54) INCREASED STRESS TOLERANCE AND ENHANCED YIELD IN PLANTS

(75) Inventors: Bala Rathinasabapathi, Gainesville, FL (US); Walid Mohamed Fouad, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 108 days.

(21) Appl. No.: 12/633,213

(22) Filed: Dec. 8, 2009

(65) Prior Publication Data

US 2010/0146665 A1    Jun. 10, 2010

Related U.S. Application Data

(62) Division of application No. 10/588,043, filed as application No. PCT/US2005/009047 on Mar. 17, 2005, now abandoned.

(60) Provisional application No. 60/554,041, filed on Mar. 17, 2004.

(51) Int. Cl.
| | |
|---|---|
| *A01H 1/00* | (2006.01) |
| *C07H 21/04* | (2006.01) |
| *C07K 14/245* | (2006.01) |
| *C12N 15/00* | (2006.01) |
| *C12N 15/82* | (2006.01) |

(52) U.S. Cl.
USPC ........... 800/278; 435/6.1; 435/69.1; 435/468; 435/419; 435/320.1; 435/183; 530/370; 536/23.2; 536/23.6; 800/295

(58) Field of Classification Search
USPC .............. 435/6.1, 6.18, 69.1, 468, 183, 419; 530/370; 536/23.2, 23.6; 800/278, 295
See application file for complete search history.

(56) References Cited

U.S. PATENT DOCUMENTS

| | | |
|---|---|---|
| 4,956,282 A | 9/1990 | Goodman et al. |
| 6,184,007 B1 | 2/2001 | Dusch et al. |
| 6,696,561 B1 | 2/2004 | Pompejus et al. |

OTHER PUBLICATIONS

Fouad et al., Plant Biology, Jul. 25, 2003 to Jul. 30, 2003, Abstract #1012, Poster #62.*
Dusch et al. Expression of the *Corynebacterium glutaminicum* panD Gene Encoding L-Aspartate-alpha-Decarboxylase Leads to Pantothenate Overproduction in ExcherichiaColi. Applied and Environmental Microbiology, Apr. 1999, vol. 65, No. 4, pp. 1530-1539.
Fouad et al. Expression of Bacterial L-aspartate-α decarboxylase in Tobacco Increases β-Alanine and Panothenate Levels and Improves Thermotolerance. Plant Molecular Biology, Mar. 2006, vol. 60, pp. 495-505.

* cited by examiner

*Primary Examiner* — Phuong Bui
(74) *Attorney, Agent, or Firm* — Timothy H. Van Dyke; Beusse, Wolter, Sanks, Mora & Maire, P.A.

(57) ABSTRACT

The present invention provides methods and compositions for improving biomass, as well as, the drought resistance of plants. More specifically, the present invention utilizes expression of aspartate carboxylase in plants and plant cells.

8 Claims, 12 Drawing Sheets

```
1    atgattcgca cgatgctgca gggcaaactc caccgcgtga aagtgactca tgcggacctg
61   cactatgaag gttcttgcgc cattgaccag gattttcttg acgcagccgg tattctcgaa
121  aacgaagcca ttgatatctg gaatgtcacc aacggcaagc gtttctccac ttatgccatc
181  gcggcagaac gcggttcgag aattatttct gttaacggtg cggcggccca ctgcgccagt
241  gtcggcgata ttgtcatcat cgccagcttc gttaccatgc cagatgaaga agctcgcacc
301  tggcgaccca acgtcgccta ttttgaaggc gacaatgaaa tgaaacgtac cgcgaaagcg
361  attccggtac aggttgcttg a
```

FIG. 15 (SEQ. ID NO: 1)

```
1    MIRTMLQGKL HRVKVTHADL HYEGSCAIDQ DFLDAAGILE NEAIDIWNVT NGKRFSTYAI
61   AAERGSRIIS VNGAAAHCAS VGDIVIIASF VTMPDEEART WRPNVAYFEG DNEMKRTAKA
121  IPVQVA
```

FIG. 16 (SEQ. ID NO: 2)

001.jpg

SEQUENCE LISTING

```
<160> NUMBER OF SEQ ID NOS: 6

<210> SEQ ID NO 1
<211> LENGTH: 381
<212> TYPE: DNA
<213> ORGANISM: Escherichia coli

<400> SEQUENCE: 1
atgattcgca cgatgctgca gggcaaactc caccgcgtga aagtgactca tgcggacctg      60
cactatgaag gttcttgcgc cattgaccag gattttcttg acgcagccgg tattctcgaa     120
aacgaagcca ttgatatctg gaatgtcacc aacggcaagc gtttctccac ttatgccatc     180
gcggcagaac gcggttcgag aattatttct gttaacggtg cggcggccca ctgcgccagt     240
gtcggcgata ttgtcatcat cgccagcttc gttaccatgc cagatgaaga agctcgcacc     300
tggcgaccca acgtcgccta ttttgaaggc gacaatgaaa tgaaacgtac cgcgaaagcg     360
attccggtac aggttgcttg a                                                381

<210> SEQ ID NO 2
<211> LENGTH: 126
<212> TYPE: PRT
<213> ORGANISM: Escherichia coli

<400> SEQUENCE: 2

Met Ile Arg Thr Met Leu Gln Gly Lys Leu His Arg Val Lys Val Thr
  1               5                  10                  15

His Ala Asp Leu His Tyr Glu Gly Ser Cys Ala Ile Asp Gln Asp Phe
             20                  25                  30

Leu Asp Ala Ala Gly Ile Leu Glu Asn Glu Ala Ile Asp Ile Trp Asn
         35                  40                  45

Val Thr Asn Gly Lys Arg Phe Ser Thr Tyr Ala Ile Ala Ala Glu Arg
     50                  55                  60

Gly Ser Arg Ile Ile Ser Val Asn Gly Ala Ala Ala His Cys Ala Ser
 65                  70                  75                  80

Val Gly Asp Ile Val Ile Ile Ala Ser Phe Val Thr Met Pro Asp Glu
             85                  90                  95

Glu Ala Arg Thr Trp Arg Pro Asn Val Ala Tyr Phe Glu Gly Asp Asn
```

-continued

```
                100                 105                 110
Glu Met Lys Arg Thr Ala Lys Ala Ile Pro Val Gln Val Ala
        115                 120                 125

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgagctcga cagggtagaa aggtaga                                      27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccccatgggg gataacaatc aagcaacc                                     28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcatgattcg cacgatgctg ccagg                                        25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagctgagca acctgtaccg gaatcgc                                      27
```

INCREASED STRESS TOLERANCE AND ENHANCED YIELD IN PLANTS

RELATED APPLICATIONS

This application is a divisional of U.S. Ser. No. 10/588,043 filed Aug. 1, 2006, now abandoned, which is a national stage filing of PCT/US05/009047 filed Mar. 17, 2005, which claims priority of U.S. Ser. No. 60/554,041 filed Mar. 17, 2004.

GOVERNMENT SUPPORT

This invention was made through support from the USDA-Agricultural Research Service, Grant No. NRICGP 2001-35318-10947. The government has certain rights in this invention.

BACKGROUND

The non-protein amino acid β-alanine is a precursor of pantothenate (vitamin B5) in all plants; and the osmoprotectant β-alanine betaine in most members of Plumbaginaceae (Hanson et. al., 1991). β-Alanine betaine is a product of three sequential methylations of β-alanine (Rathinasabapathi et. al., 2001). While beta-alanine itself can be an osmoprotectant, in certain plants it is methylated to a more effective osmoprotectant called beta-alanine betaine.

Bacteria make beta-alanine by decarboxylating aspartic acid. In *Escherichia coli*, this reaction is catalyzed by the product of panD gene encoding L-aspartate-α-decarboxylase. Aspartate decarboxylation reaction is not known in plants. Plants appear to use a variety of other ways to synthesize beta-alanine. Thus, engineering strategies to increase β-alanine pool in plants has potential applications for improving nutritional quality, yield and abiotic stress tolerance of crops.

SUMMARY

It is an object of the present invention to provide methods and compositions for increasing stress tolerance in plants.

It is another object of the present invention to provide plants and plant cells which have increased stress resistance.

It is a further object of the present invention is to increase biomass yield in plants. Preferably, enhanced biomass yield is accomplished by increasing leaf carbon dioxide concentration. Preferably still, enhanced growth and biomass is achieved by transforming plants with a polynucleotide molecule that decarboxylates aspartic acid.

Another object of the present invention is to enhance production of pantothenate in select plants.

The objects of the present invention, and others, may be accomplished with a method of increasing stress resistance in a plant, comprising expressing an aspartate decarboxylase in the plant. More preferred, an embodiment of the invention pertains to transforming plants with the panD gene of *E. coli*. (SEQ. ID NO: 1)

The objects of the present invention may also be accomplished with a method of increasing stress resistance in a plant cell, comprising expressing an aspartate decarboxylase in the plant cell.

The objects of the present invention may also be accomplished with a plant or a plant cell transformed with a nucleic acid, which encodes an aspartate decarboxylase.

Thus, the present invention also provides a method of producing such a plant or plant cell, by transforming a plant or plant cell with the nucleic acid which encodes the aspartate decarboxylase.

The present invention also provides an isolated and purified aspartate decarboxylase having the amino acid sequence of SEQ ID NO: 2.

The present invention also provides a method of producing the aspartate decarboxylase described above, comprising culturing host cells which have been transformed with a nucleic acid encoding the aspartate decarboxylase under conditions in which the aspartate decarboxylase is expressed, and isolating the aspartate decarboxylase.

In another embodiment, the present invention provides an isolated and purified enzyme having aspartate decarboxylase activity, wherein the amino acid sequence of the enzyme has a homology of from 70% to less than 100% to SEQ ID NO: 2.

The present invention also provides a method of producing the enzyme described above, comprising culturing host cells, which have been transformed with a nucleic acid encoding the enzyme under conditions in which the enzyme is expressed, and isolating the enzyme.

BRIEF DESCRIPTION OF THE DRAWINGS

FIG. 15. SEQ ID NO: 1, pertaining to accession no. L17086 (Merkel and Nichols, 1996).

FIG. 16. SEQ ID NO: 2 polypeptide molecule having aspartate carboxylase activity.

DETAILED DESCRIPTION

Figure 1:
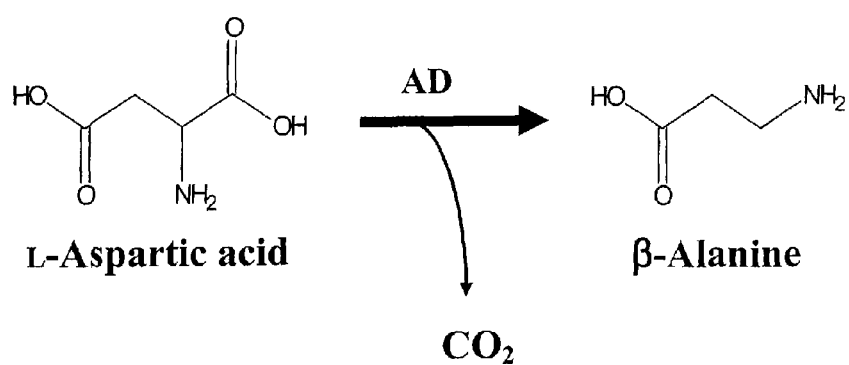
FIG. 1. Diagram showing the generation of β-alanine through the α-decarboxylation of L-aspartic acid by the bacterial L-aspartate-α-decarboxylase (ADC).

As described herein, transformation and expression of aspartate decarboxylase in plant cells and plants produces increased biomass yield. Such plants are also expected to be also more resistant to drought, heat stress, salt stress and freezing stress.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein.

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. Preferred plants include rice, corn, wheat, cotton, peanut, and soybean. Thus, in one embodiment of the present invention, the stress tolerance of a plant can be enhanced or increased by increasing the amount of protein available in the plant, preferably by the enhancement of the aspartate decarboxylase gene in the plant.

Thus, one embodiment of the present invention are plant cells carrying a polynucleotide that encodes an aspartate decarboxylase, and preferably transgenic plants carrying such polynucleotide.

As used herein, the term "enhancement" means increasing the intracellular activity of one or more enzymes in a plant cell and/or plant which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant enzyme with a high activity. Preferably the corresponding enzyme has a greater activity than the native form of the enzyme, more preferably at least in the range of 5, 10, 25% or 50% more activity, most preferably more than twice the activity of the native enzyme.

In the context of the present application, a polynucleotide sequence is "homologous" with the sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence disclosed in (Gish and States, 1993); wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, the protein may be from 70% up to less than 100% homologous to SEQ ID NO: 2.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to plant cells or plants transformed with polynucleotides which contain the complete gene with the polynucleotide sequence corresponding to the E. coli panD gene (Merkel and Nichols, 1996) or fragments thereof, and which can be obtained by screening by means of the hybridization of a corresponding gene bank with a probe which contains the sequence of said polynucleotide molecule or a fragment thereof, and isolation of the DNA sequence.

Polynucleotide sequences according to the invention are suitable as hybridization probes for RNA, cDNA and DNA, in order to isolate those cDNAs or genes which exhibit a high degree of similarity to the sequence of the panD gene.

Polynucleotide sequences according to the invention are also suitable as primers for polymerase chain reaction (PCR) for the production of DNA which encodes an enzyme having aspartate decarboxylase activity.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides for use in accord with the teachings herein include polypeptides corresponding to E. coli aspartate decarboxylase, and also includes those, at least 70% of which, preferably at least 80% of which, are homologous with the polypeptide corresponding to E. coli aspartate decarboxylase, and most preferably those which exhibit a homology of least 90% to 95% with the polypeptide corresponding to E. coli aspartate decarboxylase and which have aspartate decarboxylase activity. Thus, the polypeptides may have a homology of from 70% to up to 100% with respect to E. coli aspartate decarboxylase.

The invention also relates to transforming plant cells and plants with polynucleotide sequences which result from E. coli panD gene by degeneration of the genetic code. In the same manner, the invention further relates to DNA sequences which hybridize with E. coli panD gene or with parts of E. coli panD gene. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize the function.

In the same manner, the present invention also relates to employing DNA sequences which hybridize with E. coli panD gene or with parts of E. coli panD gene. Finally, the present invention relates to DNA sequences which are produced by polymerase chain reaction (PCR) using oligonucleotide primers which result from E. coli panD gene. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267-284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5°

C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolate polynucleotides which are substantially similar to the present polynucleotides utilized in accord with the teachings herein. In so isolating such a polynucleotide, the polynucleotide can be used as the present polynucleotide in, for example, increasing the abiotic stress and/or biomass yield of a plant.

One embodiment of the present invention is methods of screening for polynucleotides which have substantial homology to the polynucleotides of the present invention, preferably those polynucleotides encode a protein having aspartate decarboxylase activity.

The polynucleotide sequences of the present invention can be carried on one or more suitable plasmid vectors, as known in the art for plants or the like.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

In another preferred embodiment the polynucleotide comprises *E. coli* panD gene, polynucleotides which are complementary to *E. coli* panD gene, polynucleotides which are at least 70%, 80% and 90% identical to *E. coli* panD gene; or those sequence which hybridize under stringent conditions to *E. coli* panD gene, the stringent conditions comprise washing in 5×SSC at a temperature from 50 to 68° C. Thus, the polynucleotide may be from 70% up to less than 100% identical to *E. coli* panD gene.

In another preferred embodiment the polynucleotides of the present invention are in a vector and/or a host cell. Preferably, the polynucleotides are in a plant cell or transgenic plant. Preferably, the plant is selected from the group consisting of wheat, corn, peanut cotton, oat, tobacco, and soybean plant. In a preferred embodiment, the polynucleotides are operably linked to a promoter, preferably an inducible promoter designed for expression in plants.

In another preferred embodiment, the present invention provides a method for making aspartate decarboxylase protein, comprising culturing the host cell carrying the polynucleotides of the invention for a time and under conditions suitable for expression of aspartate decarboxylase, and collecting the aspartate decarboxylase protein.

In another preferred embodiment, the present invention provides a method of making a transgenic plant comprising introducing the polynucleotides of the invention into the plant.

In another preferred embodiment, the present invention provides method of increasing the abiotic stress tolerance of a plant in need thereof, comprising introducing the polynucleotides of the invention into said plant.

In another preferred embodiment, the present invention provides method of increasing the biomass yield of a plant, comprising introducing the polynucleotides of the invention into said plant under conditions where said polynucleotides are expressed.

Methods, vectors, and compositions for transforming plants and plant cells in accordance with the invention are well-known to those skilled in the art, and are not particularly limited. For a descriptive example see Karimi et al., TRENDS in Plant Science, Vol. 7, No. 5, May 2002, pp. 193-195, incorporated herein by reference.

Examples of plant species suitable for transformation with the polynucleotides and methods of the present invention include but are not limited to tobacco (*Nicotiana tabacum*), potato (*Solanum tuberosum*), soybean (glycine max), tomato (*Lycopersicon esculentum*), cassava (*Manihot esculenta*), beets, peanuts (*Arachis hypogaea*), cotton (*Gossypium hirsutum*), citrus trees (*Citrus* spp.), corn or maize (*Zea mays*), beans (e.g., green beans (*Phaseolus vulgaris*) and lima beans (*Phaseolus limensis*)), peas (*Lathyrus* spp.), sugarbeet, sunflower, carrot, celery, flax, cabbage and other cruciferous plants, pepper, strawberry, lettuce, alfalfa, oat, wheat, rye, rice, barley, sorghum and canola.

The ability to increase the biomass or size of a plant according to certain invention embodiments would have several important commercial applications. Crop species may be generated that produce higher yields on larger cultivars, particularly those in which the vegetative portion of the plant is edible. For example, increasing plant leaf biomass may increase the yield of leafy vegetables for human or animal consumption. Additionally, increasing leaf biomass can be used to increase production of plant-derived pharmaceutical or industrial products. By increasing plant biomass, increased production levels of the products may be obtained from the plants. Tobacco leaves, in particular, have been employed as plant factories to generate such products. Furthermore, it may be desirable to increase crop yields of plants by increasing total plant photosynthesis. An increase in total plant photosynthesis is typically achieved by increasing leaf area of the plant. Additional photosynthetic capacity may be used to increase the yield derived from particular plant tissue, including the leaves, roots, fruits or seed. In addition, the ability to modify the biomass of the leaves may be useful for permitting the growth of a plant under decreased light intensity or under high light intensity. Modification of the biomass of another tissue, such as roots, may be useful to improve a plant's ability to grow under harsh environmental conditions, including drought or nutrient deprivation, because the roots may grow deeper into the ground. Increased biomass can also be a consequence of some strategies for increased tolerance to stresses, such as drought stress. Early in a stress response plant growth (e.g., expansion of lateral organs, increase in stem girth, etc.) can be slowed to enable the plant to activate adaptive responses. Growth rate that is less sensitive to stress-induced control can result in enhanced plant size, particularly later in development. See U.S. Patent Publication No. 2004/0128712 which is incorporated herein by reference.

Example 1

Aspartate α-decarboxylation

Prokaryotes have a unique route of β-alanine synthesis through the α-decarboxylation of L-aspartic acid (FIG. 1). The enzyme catalyzing this reaction, L-aspartate-α-decarboxylase (ADC) was identified (Cronan, 1980), and the *Escherichia coli* panD gene for ADC was cloned, over-expressed, and the enzyme purified and characterized (Ramjee et. al., 1997, Albert et. al., 1998 and Chopra et. al., 2002). Based on 14C-aspartate radio labeling experiments, this enzyme was not detected in plants (Naylor et. al., 1958); and no sequence homologues are known in eukaryotes (Rathinasabapathi et. al., 2000).

Example 2

ADC Self-Processing

Figure 2:
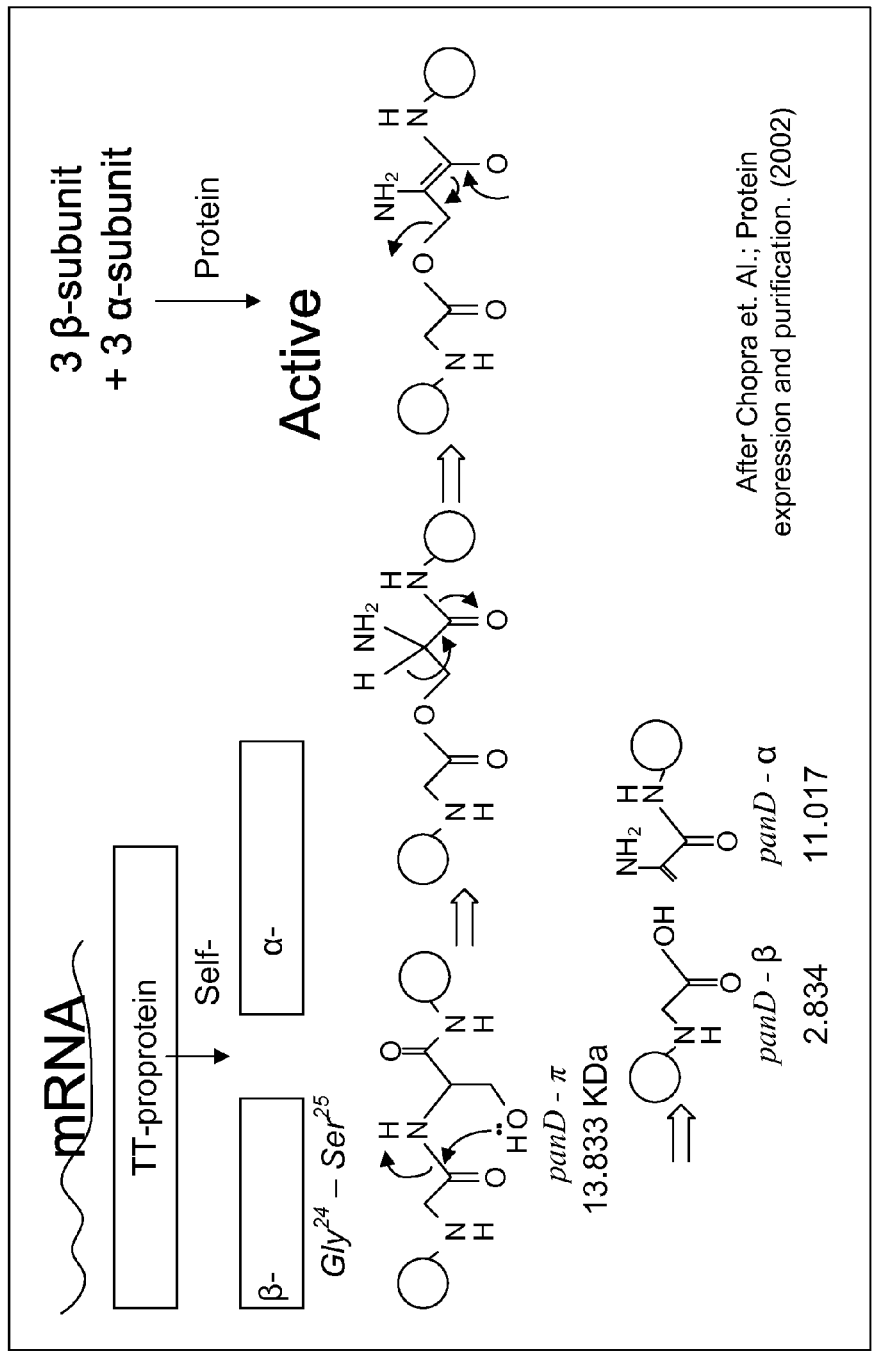
FIG. 2. ADC self-processing and assembly. Auto-cleavage between Gly24 and Ser25 amino acid residue generates pyruvoyl active group at the α-subunit. Three α-subunits and three β-subunits assemble together with one unprocessed protein to form the active ADC.

Bacterial aspartate decarboxylase is an unusual enzyme. It translates as an inactive precursor protein which goes through self-processing to give a and β subunits (102 and 24 amino acid residues, respectively; FIG. 2). Three of each of these subunits and one unprocessed π-peptide are assembled to form the active ADC enzyme (Ramjee et. al., 1997). As an unusual prokaryotic enzyme that have no homologues in eukaryotes, an important question needs to be answered; when the bacterial ADC protein is expressed in transgenic eukaryotic systems, will it behave the same way as in prokaryotes? Will it self-process and get assembled properly to give an active enzyme? To answer these questions, the idea of expressing ADC in transgenic plants seemed to be tempting. The best tool to study the ADC at the protein level in transgenic eukaryotic system is western blot; thus, over-expressing ADC in an efficient microbial expression system could facilitate ADC purification to be used for developing its specific polyclonal antibodies.

Example 3

Cloning the panD Gene from *E. coli*

A 429 bp fragment containing the aspartate decarboxylase open reading frame (ORF) was amplified using specific primers from *E. coli* DH5α genomic DNA as a template. The PCR product was cloned using TOPO-TA cloning kit panD DNA sequence was confirmed by sequencing. The pUC-panD vector complemented an *E. coli* mutant (strain AB543) defective in β-alanine biosynthesis, which confirmed that the cloned gene is coding for an active aspartate decarboxylase enzyme. This clone was used for further sub-cloning into plant expression vectors.

Example 4

Tobacco Leaf Disks Transformation

*E. coli* panD gene was sub-cloned under 35S promoter in pMON-R5 plant expression vector, which has the AAC (3)-III gene that gives the transgenic plant resistance for kanamycin. The generated vector was named pMON-D-A9. The tobacco leaf-disks were maintained under kanamycin selection starting from the third day after the co-cultivation with *Agrobacterium* and were sub-cultured every 2-3 weeks. No kanamycin-resistant shoots were obtained with the control treatments. A total of 10 and 29 independent putative transgenic plants were generated from the leaf disks infected with *Agrobacterium* harboring pMON-R5 and pMON-D-A9 vectors respectively. All these plants were maintained under kanamycin till the rooting stage and then moved to the soil.

Figure 3:
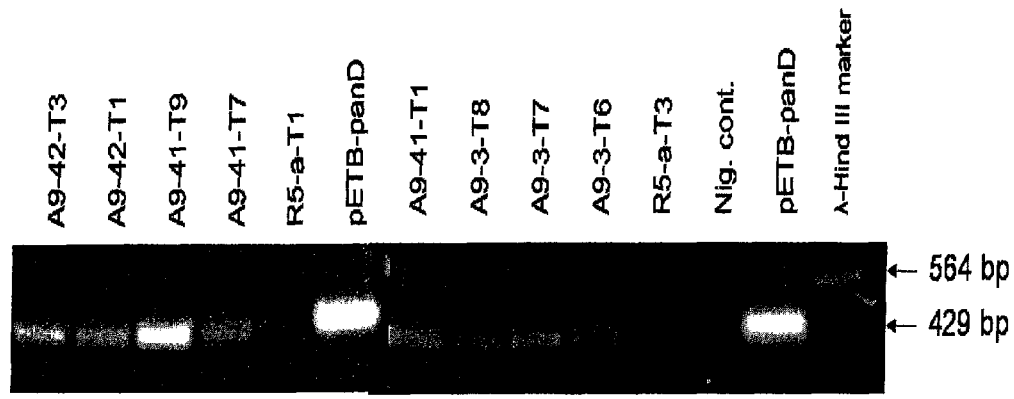
FIG. 3. PCR screening for eight pMON-panD putative transgenic plants and two pMON-R5 putative transgenic plants. Two positive control TOPO-panD vector and one negative control no DNA.
Figure 4:
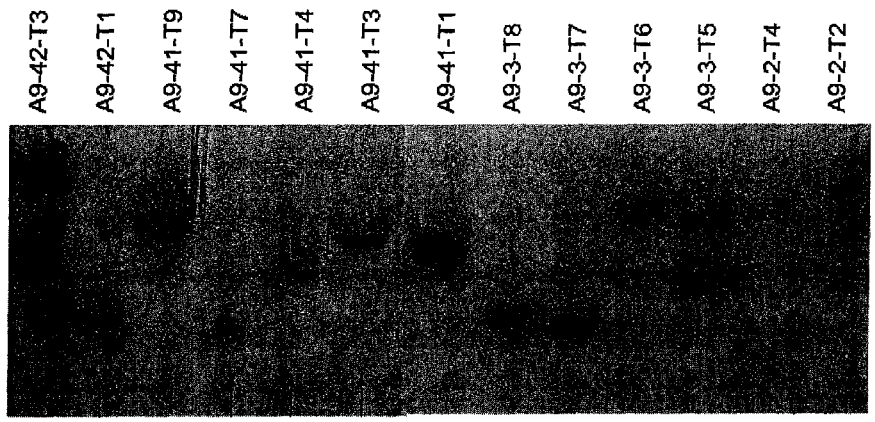
FIG. 4. Southern blot analysis for transgenic tobacco lines. 10 μg genomic DNA was digested with Hind III and hybridized with 32P-panD probe. Seven transgenic plants had a single gene insertion arrows indicate lines with single gene insertion pattern.

Genomic DNA from putative panD and pMON-R5 transgenic tobacco plants were isolated for PCR screening with panD specific primers. All the panD putative transgenic plants were positive and amplified the expected 429 bp PCR product confirming the panD insertion, while there was no PCR product with two pMON-R5 transgenic plants (FIG. 3). To know the number of insertions in each transgenic plant, Southern analysis was conducted. Seven transgenic plants out of the thirteen tested showed a pattern consistent with a single gene insertion (FIG. 4). Kanamycin-resistant phenotype segregation in F2 of transgenic lines confirmed the single gene insertion.

Figure 5:
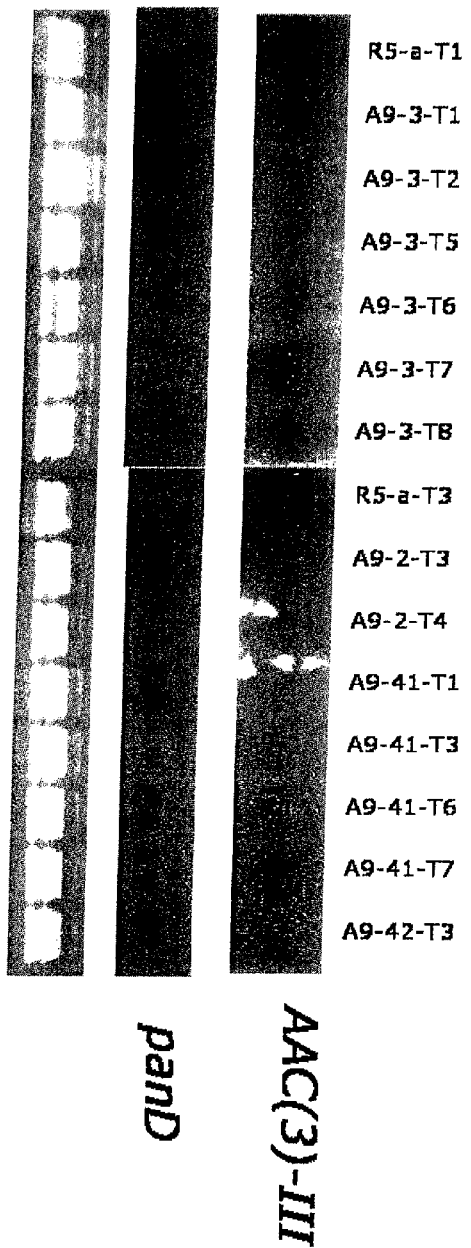
FIG. 5. Tobacco transgenic lines with different levels of AAC(3)-III and panD transcription. The lower panel shows ethidium bromide stained gel with equal load (20 μg total RNA each lane)

Total RNA from 22 panD and 4 pMON-R5 putative transgenic plants were analyzed in RNA blots, probed with 32P-labeled DNA of either AAC (3) III (kanamycin resistance gene) or panD. As expected all the samples were positive for AAC (3) III expression. Some of the transgenics had detectable levels of panD expression. The expression levels for the two genes were variable between lines (FIG. 5).

Example 4

ADC Purification using pET Blue-2 Expression System

The panD gene was amplified with introducing BspH I site on the ATG start codon at the 5' end and Pvu II site at the 3' end primers. The PCR product was digested with the two restriction enzymes and cloned directly into Nco I, Pvu II digested pET Blue-2 vector. The panD sequence was placed between the ribosomal binding site right before the panD ATG without any extra amino acids residues and a fusion peptide at the 3' end that had a His-tag. The resulting vector was named pETB-panD and sequenced. The vector was introduced to BL21-DE3 strain for protein induction with IPTG.

Figure 6:
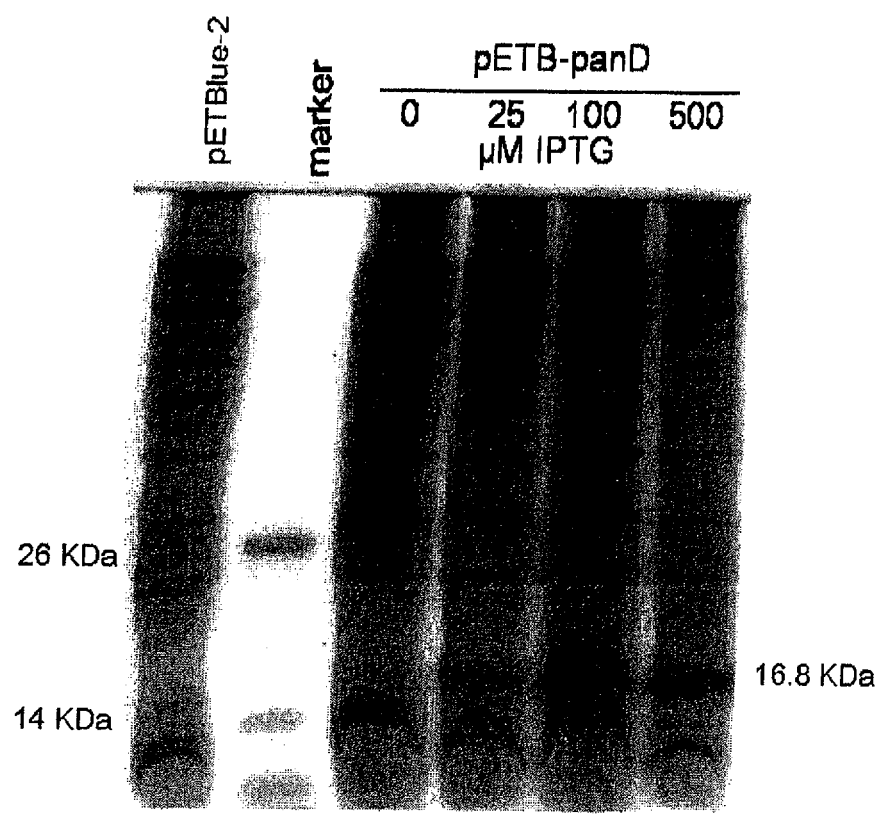
FIG. 6. ADC induction. *E. coli* strain BL21-DE3 harboring pETB-panD vector was induced for 3 h with different IPTG concentrations showing over-expression of recombinant ADC at 16.8 KDa.

FIG. 6 representing SDS-PAGE for DE3:pETB-panD induction with different IPTG concentrations for 3 h. The level of ADC expressed at molecular weight of 16.8 KDa is positively correlated to the IPTG concentration. The absence of lower band at 14 KDa suggests that the protein was not processed under the conditions of the experiment. The induced protein was also recognized with anti-His-COOH specific monoclonal antibody.

Figure 7:
FIG. 7. ADC purification. Left, 10-20% Tris-tricine gel for the DEAE-Sepharose collected fractions. Right, Western blot for the DEAE-sepharose fractions using anti-His-CooH antibody. The antibody recognized the unprocessed π-peptide (16.8 KDa) and the α-subunit (14 KDa) of the ADC.

For protein purification, DE3:pETB-panD strain was grown in LB media and when reached 0.8 OD600 the culture was induced with 100 μM IPTG for 3 hours. The harvested cells were extracted with Bug Buster Protein extraction Reagent (Novagen) and the soluble protein was loaded onto 5 ml Ni++ column (Pro Bond purification system, Invitrogen) and eluted with 250 mM Imidazole. The eluted protein was loaded onto 2 ml of DEAE-Sepharose column. The proteins were eluted with liner gradient (0-1M KCl), protein fractions separated on SDS-PAGE and blotted proteins were subject to western analysis (FIG. 7) using Anti-His-CooH monoclonal antibody (Novagen). The fractions have the recombinant ADC (F-4 and F-5) was assayed for enzyme activities and used for developing ADC native and SDS-denatured polyclonal antibodies.

Example 5

*E. coli* panD Gene is Expressed in Transgenic Tobacco

Figure 8:
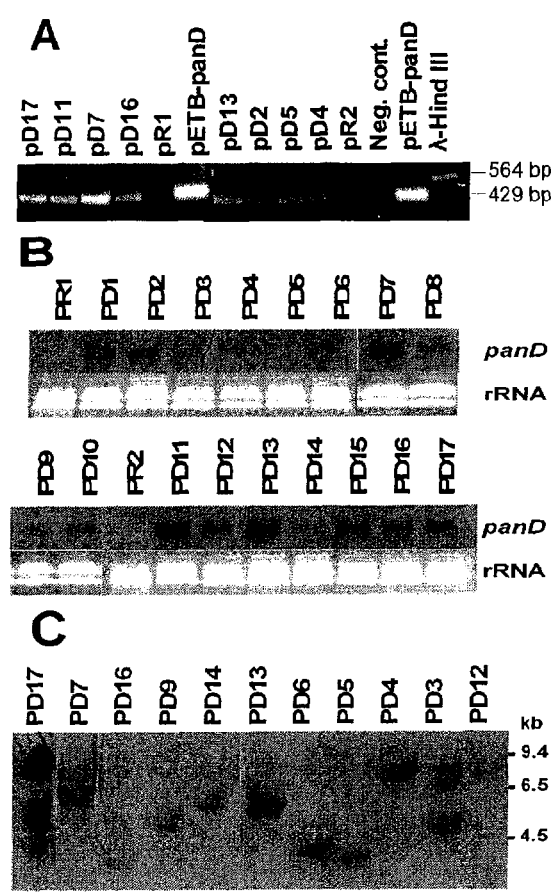
FIG. 8. Transgene integration and RNA expression in primary transgenic tobacco. (A) PCR amplification of panD sequence from tobacco genomic DNA, pETB-panD is a positive control. (B) RNA blot probed with panD DNA probe (top) and EtBr stained RNA gel showing equal load (lower panel). (C) DNA blot probed with panD DNA probe. pR and pD lines are primary transgenic lines containing pMON-R5 and pMON-R5-panD respectively.

Tobacco was transformed with *Agrobacterium tumefaciens* strain ABI carrying (pMON-R5) vector or pMON-R5- panD, which contained E. coli panD gene under the control of CaMV 35S promoter and NOS3' terminator. A total of 10 and 29 independent putative transformants were obtained for pMON-R5 and pMON-R5-panD constructs respectively based on their kanamycin resistance. In a PCR screen using genomic DNA template and primers specific for the PanD gene, all the panD putative transgenic plants amplified the expected 429 bp band which was not present in vector controls (FIG. 8A).

Total RNA from 22 panD and 4 pMON-R5 transformants were analyzed in RNA blots, probed with $^{32}$P-labeled panD DNA. Fifteen panD transformants showed low, moderate or high levels of the expected 1 Kb transcript which was absent in the vector controls (pRl; FIG. 8B). Some transformants with high level of panD transcript were analyzed by a Southern blot to determine the panD copy number. Genomic DNA, digested with Hind III, was separated on an agarose gel and blotted on nitrocellulose and probed with a panD-specific DNA probe. The panD gene sequence does not have a Hind III site but there is a Hind III site upstream of the CaMV 35S promoter. Eight panD transformants showed a single band, consistent with a single panD gene insertion (FIG. 8C).

Some of the transformants with single panD gene per genome based on DNA blot analysis and positive for gene expression based on RNA blots were grown in a greenhouse and selfed. The progeny from these plants segregated 3:1 for kanamycin resistance: sensitivity in a seedling bioassay, consistent with the single gene insertion (data not shown). Further analyses were done on two lines homozygous for the panD transgene (pD2 and pD7) and a vector control line (pR5) homozygous for the kanamycin resistance gene.

Example 6

E. coli ADC Protein Expressed in Transgenic Tobacco is Active

Figure 9:
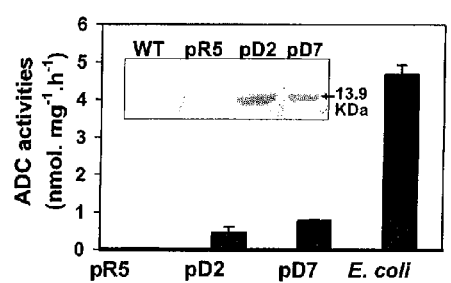
FIG. 9. Expression of ADC protein in two transgenic lines homozygous for the *E. coli* panD gene. Specific activities of ADC in protein extracts. Inset: Western blot probed with *E. coli* ADC-specific polyclonal antibodies. WT=Wild-type, pR5=Vector control, pD2 and pD7=panD transgenic homozygous lines, E. coli strain=BL21-DE3.

Protein extracts from the leaves of pD2 and pD7 showed detectable activities for ADC (FIG. 9) and little activity was present in extracts from the pR5 transgenic line (FIG. 9). The ADC activity in the PEG-concentrated crude protein extracted from transgenic lines pD2 and pD7 was 465 and 793 pmol g$^{-1}$ h$^{-1}$ respectively. However, in crude protein extract from E. coli BL21-DE3 strain, the ADC specific activity was around 6-10× more than the transgenic lines pD2 and pD7 (FIG. 9). In immunoblots with ADC-specific polyclonal antibodies, a band corresponding to 13.9 kDa, the unprocessed protein was revealed (FIG. 9, inset). Both WT and pR5 plants did not show reaction with the ADC-specific polyclonal antibodies at 13.9 kDa. However in the two transgenic lines there was no signal for the 11.01 kDa and 2.83 kDa protein bands corresponding to α and β peptides respectively.

Example 7

Free Amino Acid Analysis in Transgenic Lines

Total free amino acids and β-ala levels in leaves were evaluated using HPLC separation of amino acid-PTC derivatives. Five week old plants were grown either at 24° C. or 35° C. for one week prior to analysis because of a thermotolerance phenotype of the panD lines (see below). At both the temperatures, pD2 and pD7 lines had higher levels of β-ala as a percent of total amino acids compared to the pR5 and WT lines (Table 1). β-Ala was about 0.4% of the total free amino acids in the control lines and about 0.6% of the total free amino acids in the pD2 and pD7 lines. Compared to the control lines, pD2 and pD7 had about 1.2-1.3× and 2-4× more absolute β ala levels at 24° C. and 35° C. respectively (Table 1). The total free amino acid level in the panD lines was also elevated about 1.8-3.7× at 35° C. but not at 24° C. (Table 1).

TABLE 1

Levels of β-ala and total free amino acids in transgenic tobacco expressing E. coli panD gene compared to vector control and wild-type. Fully expanded leaves were sampled from 6-week old seedlings either growing at 24° C. or after at 35° C. for one week right before sampling. Values are means and standard error for three independent analyses.

| Temp | Genotype | β-Ala nmol·g$^{-1}$ fwt | β-Ala % of Total amino acids | Total Free amino acid (nmol·g$^{-1}$ fwt) |
|---|---|---|---|---|
| 24° C. | WT | 17.09 ± 5.5 | 0.33 ± 0.05 | 4687 ± 965 |
|  | pR5 | 16.78 ± 1.7 | 0.37 ± 0.07 | 5023 ± 1072 |
|  | pD2 | 20.59 ± 3.2 | 0.54 ± 0.06 | 3699 ± 170 |
|  | pD7 | 21.68 ± 3.6 | 0.58 ± 0.05 | 3672 ± 502 |
| 35° C. | WT | 16.6 ± 0.1 | 0.41 ± 0.03 | 4047 ± 345 |
|  | pR5 | 26.5 ± 8 | 0.39 ± 0.03 | 6178 ± 1347 |
|  | pD2 | 66.1 ± 0.4 | 0.62 ± 0.05 | 10855 ± 816 |
|  | pD7 | 79.4 ± 10.5 | 0.59 ± 0.1 | 14891 ± 4127 |

Example 8

Transgenic Expression of ADC Improves Vegetative Biomass

Figure 10:
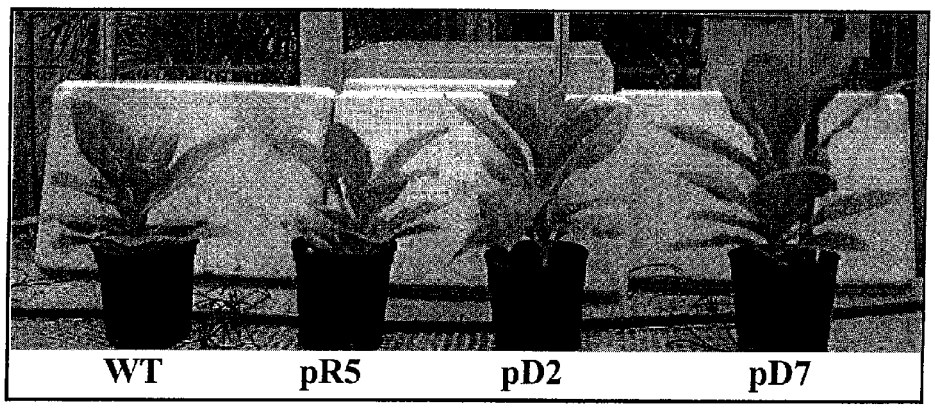
FIG. 10. Expression of E. coli panD gene in transgenic tobacco improves seedling growth. Representative of 10-week old seedlings from WT, pR5 pD2 and pD7 lines growing in the greenhouse.
Figure 11:
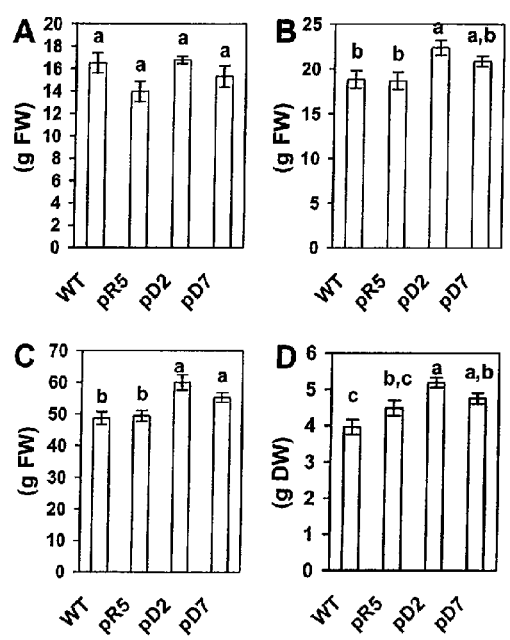
FIG. 11. Expression of E. coli panD gene in transgenic tobacco improves seedling biomass. (A) Aerial biomass, fresh weight, of plants germinated and grown at 24° C. for six weeks. (B) Aerial biomass, fresh weight, of plants grown at 30° C. for one week after five weeks of growth at 24° C. Aerial biomass: fresh weight (C), dry weight (D) of plants grown at 30° C. for four weeks after five weeks of growth at 24° C. WT=Wild-type, pR5=Vector control, pD2 and pD7=panD transgenic homozygous lines. Data are means (±S.E.) from six plants.

In general, young seedlings of pD2 and pD7 lines were larger than the pR5 and WT plants from visual inspection. FIG. 10 shows 10-week old seedlings representing pD2, pD7, pR5 and WT lines, grown in a greenhouse (20/35° C. min/max temperatures). In a controlled temperature experiment to evaluate growth, seeds were germinated and the seedlings maintained at 24° C. for five weeks prior to transferring to environmental growth chambers set at either 24° C. or 30° C. The aerial biomass was evaluated after one week and four weeks. While there were no significant differences between the four genotypes at 24° C. (FIG. 11A), pD2 and pD7 lines had higher mean aerial biomass compared to pR5 and WT lines when grown at 30° C. for a week (FIG. 11B). This increase, which ranged between 11.2 and 19.2% compared to the WT, however was not statistically significant for pD7 line (FIG. 11B). When plants were grown for additional three weeks at 30° C., lines pD2 and pD7 had significantly higher (P≤0.05) mean aerial fresh weight (FIG. 11C). Line pD2 had significantly greater (P≤0.05) dry weight compared to the controls (FIG. 11D). The increase in the biomass was on an average 17.4% and 18.7% fresh and dry weights respectively, greater than the control lines.

Example 9

Thermotolerance Phenotype in Transgenic Lines

Figure 12:
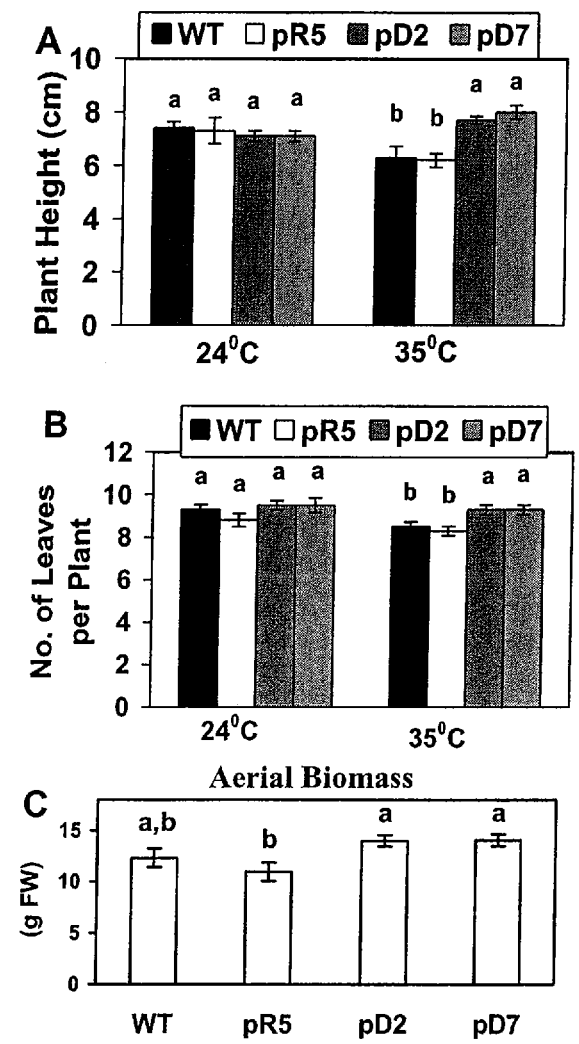
FIG. 12. Expression of E. coli panD gene in transgenic tobacco improves growth and biomass under high temperature. Five week old seedlings from wild-type, pR5, pD2 and pD7 lines were grown at 24° C. and 35° C. for one week and harvested for plant height (A), number of leaves per plant (B), and aerial biomass (C). Aerial biomass data for plants at 24° C. are shown in FIG. 3.B. Data are means (±S.E.) from six plants.
Figure 13:
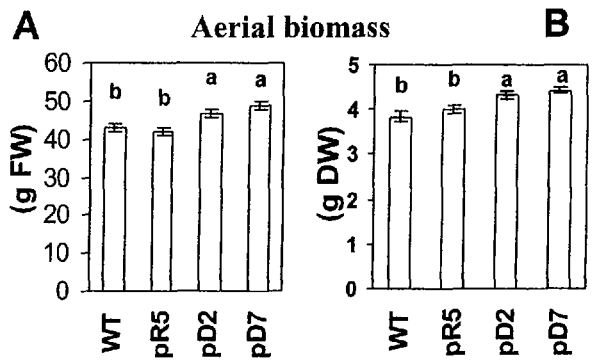
FIG. 13. Expression of E. coli panD gene in transgenic tobacco improves plants' recovery from heat stress. Five week old seedlings from wild-type, pR5, pD2 and pD7 lines were stressed for one week at 35° C. and then allowed to recover for three weeks at 30° C. and harvested for aerial biomass fresh weight (A) and dry weight (B). Data are means (±S.E.) from six plants.

To study the high temperature stress effect on transgenic lines, seeds were germinated and seedlings maintained at 24° C. for five weeks and then transferred to environmental growth chambers set at 35° C. After one week of high temperature stress, WT and pR5 plant's height was reduced by 14.8 and 15.1% respectively compared to plants growing at 24° C. (FIG. 12A). On the other hand, pD2 and pD7 lines gained 8 and 12% greater height at 35° C. compared to plants growing at 24° C. (FIG. 12A). The pR5 and WT plants at 35° C. showed significant reduction in their leaf number compared to plants growing at 24° C. while pD2 and pD7 did not (FIG. 12B). The pD2 and pD7 lines had also higher aerial biomass compared to WT and pR5 lines, however this increase in the biomass was not statistically significant when plants were evaluated after one week of growth at 35° C. (FIG. 12C). In another experiment, the plants were stressed for one week at 35° C. and then were allowed to recover for three weeks at 30° C. The pD2 and pD7 lines gained significantly ($P \leq 0.05$) greater aerial biomass compared to WT and pR5 lines (FIG. 13). The mean increases in fresh and dry weights were 12.5% and 11.2% respectively higher than that achieved by the pR5 and WT plants during recovery from high temperature stress (FIG. 13).

Example 10

Transgenic Expression of ADC Improves Tobacco Seed Germination at 42° C.

Figure 14:
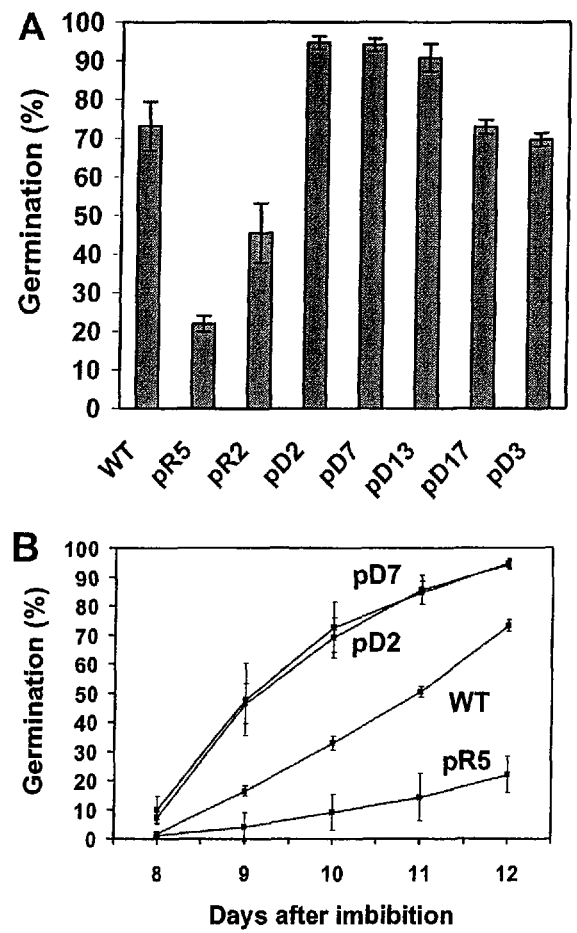
FIG. 14. Expression of E. coli panD gene in transgenic tobacco improves germination rate and percent germination at 42° C. (A) Germination percent at 42° C. at day 12 after sowing. (B) Germination percent at 42° C. scored over 12 d after sowing. WT, pR vector control, pD=panD transgenic lines. Data are means (±S.E.) from six independent Petri dishes.

When seeds of panD lines pD, vector control pR and wild-type seeds were germinated at 30° C., all the lines germinated equally well (data not shown). However, when the imbibed seeds were incubated at 42° C., lines expressing the panD gene germinated better than the vector controls (FIG. 14.A.). Three out of five panD lines germinated better than the wild-type also (FIG. 14A). A time course experiment at 42° C. showed that pD2 and pD7 lines had significantly higher ($P<0.05$) germination rate than the vector control and wild-type (FIG. 14B). Vector control line had significantly lower ($P<0.05$) germination rate than the wild-type at 42° C. (FIG. 14B).

Example 11

Materials and Methods for Examples 5-10

(a) Materials

Bacterial media, antibiotics, buffers, protease inhibitors and DEAE-Sepharose were from Sigma (St. Louis, Mo.). Plasmid purification and gel extraction kits were from Qiagen (Valencia, Calif.). U [$^{14}$C]-L-aspartate (217 mCi·mmol$^{-1}$) from ICN Biomedicals (Irvine, Calif.) and dGTP ($^{\alpha-32}$P, 800 Ci mmol$^{-1}$) from Amersham Bioscience (Piscataway, N.J.) were used without further purification. Gradient SDS-PAGE protein gels, protein molecular weight markers, protein stains and PVDF membranes were from BioRad (Hercules, Calif.). Bacterial expression vector pET-Blue-2 and E. coli BL21-DE3 were from Novagen (Madison, Wis.). DNA $M_r$ marker, Taq polymerase, dNTPs, restriction enzymes, pCR 2.1-TOPO cloning kit, TRIzol reagent, Pro-Bond Ni-NTA resin, and secondary antibodies were from Invitrogen (Carlsbad, Calif.). Oligonucleotide primers were synthesized by the custom primer synthesis unit of Invitrogen (Carlsbad, Calif.).

(b) Construction of the Expression Vector

E. coli panD open reading frame (ORF) with the start and stop codon (429 bp) was amplified from DH$_5\alpha$ genomic DNA using the primers 5' to 3' CCGAGCTCGACAGGGTAGAAAGGTAGA (SEQ ID NO. 3) and CCCCATGGGGATAACAATCAAGCAACC (SEQ ID NO. 4). The PCR product, cloned in pCR 2.1-TOPO vector, was verified by sequencing. A single point mutation in the clone's ORF converted Cys$_{26}$ to Tyr. This panD gene was sub-cloned in the right frame into pUC-18 vector under lac promoter. The pUC-panD vector successfully complemented an E. coli mutant defective in β-ala synthesis (ATCC Number AB354), confirming that the cloned gene coded for an active ADC.

The plant expression vector pMON979 contains a multiple cloning site (MCS) between an enhanced CaMV 35S promoter and NOS3' terminator, a kanamycin resistance selectable marker for plant selection and a spectinomycin resistance gene for bacterial selection. A 34-bp synthetic dsDNA containing BamHI, SacI, HpaI, ApaI, KpnI and EcoRI sites was ligated into the BglII and EcoRI sites of the MCS to create pMON-R5. E. coli panD ORF in TOPO-panD vector was digested with EcoRI and sub-cloned into EcoRI digested pMON-R5 plant expression vector to derive pMON-R5-panD. Recombinants with the insert in the correct orientation were identified by restriction analyses.

(c) Agrobacterium-Mediated Transformation of Tobacco

The pMON-R5-panD and pMON-R5 were transferred into Agrobacterium tumefaciens ABI strain via triparental mating (An et al., 1988). Transformation of Nicotiana tabacum cv. Havana 38 (Wisconsin 38) was performed as described previously (An et al., 1988; Rathinasabapathi et al., 1994). Putative transformants were selected based on their resistance to kanamycin (50 mg·L$^{-1}$) in the media and verified by PCR using panD specific primers.

(d) DNA and RNA Blot Analyses

Genomic DNA (20 μg), extracted using CTAB method (Wong and Taylor 1993), was digested with restriction enzymes, separated by 1.2% (wt/v) agarose gel, and transferred to nylon membranes (Sambrook et al., 1989). Total leaf RNA (20 μg), extracted using TRIzol reagent (Invitrogen, Carlsbad, Calif.), was separated in formaldehyde 1.2% (wt/v) agarose gel, and transferred to nylon membrane (Sambrook et al., 1989). Equal loading of RNA was verified by ethidium bromide staining. A 446 bp of PanD sequence was labeled with [$^{32}$P]dGTP (800 Ci mmol$^{-1}$, Amersham BioSciences) using a random primer method (Invitrogen) according to manufacturer's instructions. Hybridization, membrane washing and autoradiography were done as described (Raman and Rathinasabapathi, 2003).

(e) Genetic Analyses and Identification of Homozygous Lines

Primary transgenic lines and wild-type (WT) tobacco were grown in a greenhouse and selfed. Surface sterilized T$_2$ seeds of each line were placed on Petri plates containing half-strength MS salts media supplemented with kanamycin (200 mg·L$^{-1}$). Seeds were germinated at 24° C. under continuous light (40-50 μmol·m$^{-2}$ s$^-$) for 14 d. Seedlings were scored for their resistance to kanamycin and segregation was analyzed using a $X^2$ test. Several T$_2$ lines with single gene segregation for kanamycin resistance were grown in a greenhouse for flowering and their seeds were analyzed for the segregation of the marker. Those lines that did not segregate at T3 generation were considered homozygous.

(f) ADC Expression, Purification and Polyclonal Antibodies

The panD gene was amplified from E. coli DH$_5\alpha$ genomic DNA using primers 5' to 3' TCATGATTCGCACGATGCTGCCAGG SEQ ID NO. 5 and CAGCTGAGCAACCTGTACCGGAATCGC SEQ ID NO. 6 primers. The BspH I site was introduced on the panD ATG start codon by the forward primer and the Pvu II site was introduced at the 3' end by the reverse primer. The PCR product, generated using Advantage-HF 2 PCR Kit (Clontech; Palo Alto, Calif.) was digested with BspH I and Pvu II and ligated directly into Nco I, Pvu II digested pET-Blue-2 vector generating pET-panD. Recombinant E. coli BL21-DE3 harboring pETB-panD vector or vector control, induced with IPTG, were suspended in BugBuster reagent (Novagen; Madison, Wis.) 5 ml·g$^{-1}$ wet cells, for total soluble protein extraction. Benzonase (Novagen; Madison, Wis.) 1 μl·ml$^{-1}$, β-mercaptoethanol 5 mM final concentration and a protease inhibitor cocktail as described (Rathinasabapathi et al., 2001) were added. Affinity purification of the recombinant protein was performed according to the manufacturer's instructions of ProBond resin (Invitrogen; Carlsbad, Calif.). The sample was further purified using a 5 mL DEAE-Sepharose ion-exchange column (Sigma; St. Louis, Mo.). Following protein elution using a 0 to 0.3 M linear NaCl gradient, the purified ADC-His was detected using SDS-PAGE gels. Total protein was estimated by the method of Peterson (1977), and bovine serum albumin was the standard. The purified native ADC was used for raising polyclonal antibodies in rabbit according to manufacturer's protocol (Cocalico Biological, Reamstown, Pa.).

(g) SDS-PAGE and Immunoblot Analyses

SDS-PAGE was performed in 10% to 20% Tris-Tricine gradient PAGE gel (Bio Rad; Hercules, Calif.) or 12% (wt/v) Tris-glycine polyacrylamide gels. Protein samples were diluted with 2× of SDS-PAGE sample buffer containing 0.1 M Tris-HCl, pH 6.8, 4% wt/v SDS, 20% (v/v) glycerol, 5 mM dithiotheritol, and 0.08% (wt/v) bromophenol blue and denatured at 95° C. for 10 min. The separated proteins were visualized with Coomassie Brilliant Blue or silver stain. The SDS-PAGE separated proteins were transferred by electroblotting onto a PVDF membrane. The membranes were incubated with different dilutions of antibodies after blocking with blocking buffer (20 mM Tris-HCl, pH 7.5, 140 mM NaCl, and 5% (wt/v) nonfat dry milk). The primary anti-ADC polyclonal antibodies were used at 1:5000 dilution. The secondary anti-rabbit IgG antibody conjugated to alkaline phosphatase (Sigma, St. Louis, Mo.) was used at a 1:30000 dilution. After washing, binding of the antibody was recorded using a colorimetric substrate. The alkaline phosphatase activity was detected in 10 ml alkaline phosphatase buffer containing 0.1 M Tris-HCl pH 9, 0.1 M NaCl, 5 mM $MgCl_2$, 3.3 mg nitro blue tetrazolium and 1.7 mg bromochloroindolyl phosphate.

(h) ADC Activity Assays

Aspartate decarboxylase was assayed using a radiometric procedure employing $^{14}$C-aspartate. The assays contained in 50 mM potassium phosphate, pH 7.0, 1.2 mM of aspartate, 0.2 µCi of $^{14}$C aspartate (217 mCi·mmol$^{-1}$), 5 mM DTT, and crude protein or PEG (25% wt./v)-precipitated fraction in a total volume of 50 µL. Following incubation at 37° C. for 1 h, the reaction was terminated by adding 5 µL it of 72% (wt/v) trichloroacetic acid and the proteins were removed by centrifugation at 14000×g for 10 min. Radiolabeled $^{14}$C carbon dioxide generated by ADC was trapped during the reaction with Whatman 3 paper saturated with 20% (wt/v) KOH. At the end of the reaction period the reaction products in the reaction mixture were separated from the substrate using thin layer chromatography using cellulose plate (Selecto Scientific, Georgia, USA) developed with solvents butanol: acetic acid: water (60:15:20, v/v/v), followed by autoradiography. The product formed was quantified by isolating the zone corresponding to β-ala. In a variation of the assay, $^{14}CO_2$ trapped from the assay was quantified in 50% (v/v) Ready Gel (Beckman Instruments, Fullerton, Calif.) in a Beckman liquid scintillation counter. The counting efficiency was 30%.

(i) Germination Tests

Seeds of panD homozygous transgenic lines, vector alone transgenic and wild-type control lines were surface sterilized. Around 100 seeds of each line were placed on 100×15 mm Petri plates containing half-strength MS salts. The plates were incubated in a growth chamber set at 24° C., 30° C., 36° C. or 42° C. under continuous light (20 µmol·m$^{-2}$ s$^{-1}$). Percent germination was scored over a period of 12 d based on radical emergence.

(j) Growth Tests and High Temperature Stress

For growth analysis and temperature stress, five weeks old seedling of two homozygous transgenic lines, vector control (R5) and WT control lines growing in 350 mL pots at 24° C. were used. The growing medium was Metro-Mix 300 (Scotts-Sierra, Marysville, Ohio) supplemented with 1 g slow-release fertilizer Osmocote (N:P:K 24:6:10, 5.8% ammoniacal N, 5% nitrate N, and 13.2% urea N) per pot. The pots were irrigated to container capacity every day. Seedlings were germinated and maintained in a culture room at 24° C. under 50 µmol·m$^{-2}$ s$^{-1}$ light intensity 16 h light/8 h dark period for five weeks, then they were transferred to growth chambers adjusted at 24° C., 30° C. or 36° C. with same light period and intensity. After one week, or four weeks, aboveground biomass, plant height, and number of leaves per plant were recorded.

(k) Quantification of Free β-ala and Total Free Amino Acids

Fully expanded leaf (1.0 g fresh wt.) was extracted using a methanol:chloroform:water mixture as described previously (Hanson and Gage 1991). The aqueous fraction was evaporated under a stream of $N_2$, redissolved in water and purified using a Dowex 50-H$^+$ ion exchange resin as described previously (Rhodes et al., 1989). Following pre-column derivatization of amino acids using phenylthiocyanate (PITC), the PTC-amino acid derivatives were separated and quantified by HPLC using Waters 515 HPLC Pump, Waters 717 plus Autosampler, Waters 2410 Refractive Index Detector, and YMC-Pack ODS-AM, S-5 µm, 12 nm 250×4.6 mm I.D. column, as described (Sherwood 2001). Nor-leucine was used as the internal standard. Amino acid derivatives were identified at 254 nm based on retention times for pure standards run under identical conditions.

(l) Statistical Treatment of Data

All experiments were done at least twice with 3-6 replicates per treatment. The data were processed using the analysis of variance in a completely randomized design model using the SAS software (SAS, 2002). The mean separations were done using Duncan's multiple range test at $P \leq 0.05$.

REFERENCES

Albert A, Dhanaraj V, Genschel U, Khan G, Ramjee M K, Pulido R, Sibanda B L, Von Delft F, Witty M, Blundell T L, Smith A G, and Abell C (1998). Crystal structure of aspartate decarboxylase at 2.2 Å resolution provides evidence for an ester in protein self-processing. Nat. Struct. Biol., 5: 289-293.

An, G., Ebert, P. R., Mitra, A., Ha, S. B. (1988) Binary vectors. In *Plant molecular biology manual* (Gelvin, S. B., Schilperoort, R. A. eds). Kluwer, Dordrecht, A3: pp. 1-19.

Chopra S, Pai H, and Ranganathan A (2002). Expression, purification, and biochemical characterization of *Mycobacterium tuberculosis* aspartate decarboxylase, PanD. Protein Expr. Purif., 25: 533-540.

Cronan, J. E., Jr. (1980). Beta-alanine synthesis in *Escherichia coli*. J. Bacteriol., 141: 1291-1297.

Gish W and States D J (1993) Identification of protein coding regions by database similarity search. Nature Genetics 3:266-272.

Hanson A D, Rathinasabapathi B, Chamberlin B, Gage D A (1991). Comparative physiological evidence that β-alanine betaine and choline-O-sulfate act as a compatible osmolytes in halophytic *Limonium* species. Plant Physiol., 97: 306-310.

Merkel W K, Nichols B P (1996) Characterization and sequence of the *Escherichia coli* panBCD gene cluster, FEMS Microbiol. Lett. 143: 247-252.

Naylor N W, Rabson R, and Tolbert N E (1958). Aspartic-14C acid metabolism in leaves, roots and stems. Physiol. Plant., 11: 537-547.

Raman, S. B., and Rathinasabapathi, B. (2003) β-Alanine N-methyltransferase of *Limonium latifolium*. cDNA cloning and functional expression of a novel N-methyltransferase implicated in the synthesis of the osmoprotectant β-alanine betaine. *Plant Physiol.* 132, 1642-1651.

Ramjee M K, Genschel U, Abell C, and Smith A G (1997). *Escherichia coli* L-aspartate-α-decarboxylase: preprotein processing and observation of reaction intermediates by electrospray mass spectrometry. Biochem. J., 323: 661-669.

Rathinasabapathi, B., McCue, K. F., Gage, D. A. and Hanson, A. D. (1994) Metabolic engineering of glycine betaine synthesis: plant betaine aldehyde dehydrogenases lacking typical transit peptides are targeted to tobacco chloroplasts where they confer betaine aldehyde resistance. *Planta* 193, 155-162.

Rathinasabapathi B, Fouad W M, and Sigua C A (2001). β-Alanine Betaine Synthesis in the Plumbaginaceae. Purification and Characterization of a Trifunctional, S-Adenosyl-L-Methionine-Dependent N-Methyltransferase from *Limonium latifolium* Leaves. Plant Physiol., 126: 1241-1249.

Rathinasabapathi B, Sigua C, Ho J, Gage D A (2000). Osmoprotectant β-alanine betaine synthesis in the Plumbaginaceae: S-adenosyl-1-methionine dependent N-methylation of β-alanine via N-methyl β-alanine and N,N-dimethyl β-alanines. Physiol. Plant., 109: 225-231.

Sambrook, J., Fritsch, E. F., and Maniatis, T. (1989) Molecular cloning: A laboratory manual 2nd edn. Cold Spring Harbor Laboratory Press.

The teachings of the references cited throughout the specification are incorporated herein in their entirety by this reference to the extent they are not inconsistent with the teachings herein. It should be understood that the examples and embodiments described herein are for illustrative purposes only and that various modifications or changes in light thereof will be suggested to persons skilled in the art and are to be included within the spirit and purview of this application.

What is claimed is:

1. A method of producing an increased yield phenotype in a plant, the method comprising producing a transgenic plant expressing a nucleic acid sequence encoding an aspartate decarboxylase polypeptide, and selecting the transgenic plant having an increased yield phenotype if it has a yield greater than that of a plant having no expression of said nucleic acid sequence.

2. The method of claim 1, wherein said expressing increases freeze tolerance in said plant relative to no expression of said nucleic acid sequence.

3. The method of claim 1, wherein said aspartate decarboxylase polypeptide comprises the sequence of SEQ ID NO: 2.

4. The method of claim 1, wherein said aspartate decarboxylase polypeptide is encoded by a nucleic acid sequence having the sequence of SEQ ID NO: 1.

5. The method of claim 1, wherein the plant is selected from the group consisting of soybean, rice, tomato, wheat, corn, potato, cotton, oilseed rape, sunflower, alfalfa, clover, sugarcane, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, watermelon, and brassicas.

6. The method of claim 1, wherein the plant is selected from the group consisting of wheat, corn, peanut, cotton, oat, and soybean.

7. The method of claim 1, wherein the plant is transformed with a vector comprising said nucleic acid sequence.

8. The method of claim 1, wherein said selecting comprises selecting the transgenic plant having an increased yield phenotype if it has a yield and thermotolerance greater than that of a plant having no expression of said nucleic acid sequence.

* * * * *